United States Patent
Lee et al.

(10) Patent No.: US 10,292,969 B2
(45) Date of Patent: May 21, 2019

(54) COMPOSITION FOR PREVENTION OR TREATMENT OF BRONCHIAL ASTHMA COMPRISING PKR INHIBITOR AS ACTIVE INGREDIENT

(71) Applicants: INDUSTRIAL COOPERATION FOUNDATION CHONBUK NATIONAL UNIVERSITY, Jeonju-si, Jeollabuk-do (KR); CHONBUK NATIONAL UNIVERSITY HOSPITAL, Jeonju-si, Jeollabuk-do (KR)

(72) Inventors: Yong Chul Lee, Jeonju-si (KR); So Ri Kim, Jeonju-si (KR)

(73) Assignee: Undustrial Cooperation Foundation Chonbuk National University, Jeonju (KR)

( * ) Notice: Subject to any disclaimer, the term of this patent is extended or adjusted under 35 U.S.C. 154(b) by 35 days.

(21) Appl. No.: 15/547,030

(22) PCT Filed: Dec. 16, 2015

(86) PCT No.: PCT/KR2015/013791
§ 371 (c)(1),
(2) Date: Jul. 27, 2017

(87) PCT Pub. No.: WO2016/129802
PCT Pub. Date: Aug. 18, 2016

(65) Prior Publication Data
US 2018/0000794 A1    Jan. 4, 2018

(30) Foreign Application Priority Data

Feb. 12, 2015 (KR) ........................ 10-2015-0021423

(51) Int. Cl.
| A61K 31/429 | (2006.01) |
| A61K 31/4178 | (2006.01) |
| A61K 31/428 | (2006.01) |
| A23L 33/10 | (2016.01) |
| A23L 29/00 | (2016.01) |

(52) U.S. Cl.
CPC ............ *A61K 31/429* (2013.01); *A23L 29/00* (2016.08); *A23L 33/10* (2016.08); *A23V 2002/00* (2013.01)

(58) Field of Classification Search
CPC . A61K 31/429; A61K 31/4178; A61K 31/428
See application file for complete search history.

(56) References Cited

U.S. PATENT DOCUMENTS 8,329,646 B2 * 12/2012 Tisdale ................ A61K 31/198
514/21.91

FOREIGN PATENT DOCUMENTS

| WO | 2000035920 | 6/2000 |
| WO | 2009070378 | 6/2009 |
| WO | 2012072269 | 6/2012 |

OTHER PUBLICATIONS

Jammi, N. V. et al., "Small molecule inhibitors of the RNA-dependent protein kinase", Biochemical and Biophysical Research Communications, vol. 308, 2003, pp. 50-57.

* cited by examiner

*Primary Examiner* — Kendra D Carter
(74) *Attorney, Agent, or Firm* — Hunton Andrews Kurth LLP

(57) ABSTRACT

The present invention relates to a composition for prevention or treatment of bronchial asthma comprising a PKR inhibitor as an active ingredient. The PKR inhibitor and derivatives thereof according to the present invention can be used as a pharmaceutical for prevention, amelioration or treatment of bronchial asthma and as a supplementary health food because the PKR inhibitor and derivatives thereof reduce the total counts of inflammatory cells, eosinophils, neutrophils and lymphocytes in bronchoalveolar lavage fluid of neutrophilic severe asthma-induced mice, reduce airway inflammation and airway hyper-responsiveness, and reduce inflammatory mediators.

4 Claims, 7 Drawing Sheets

[Fig. 1]
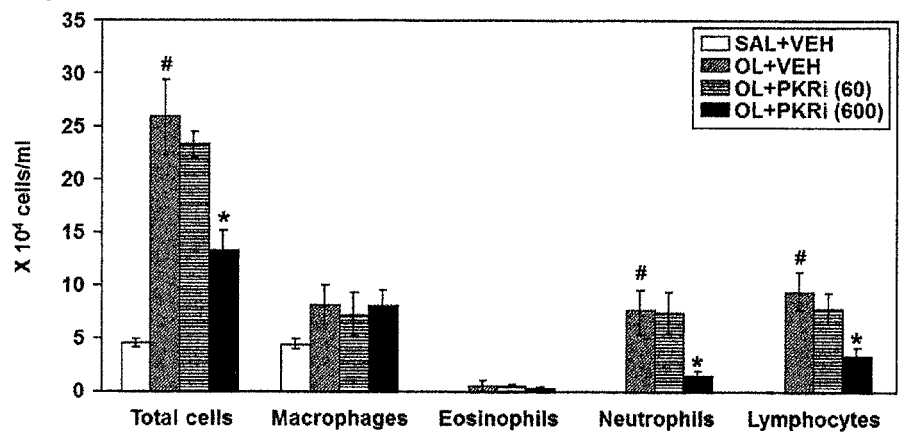
[Fig. 2]
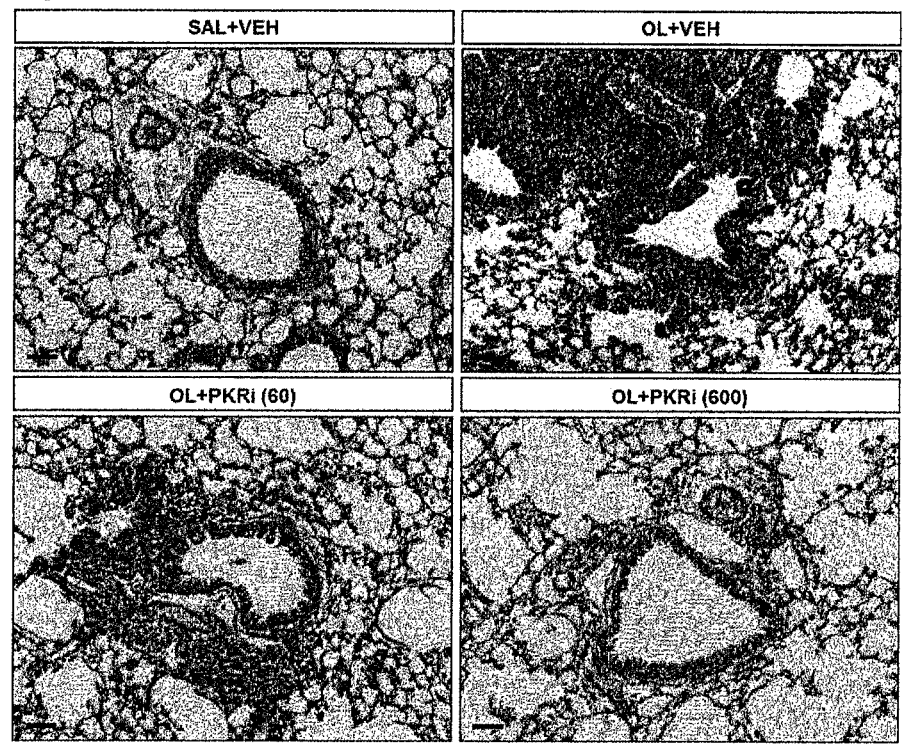

[Fig. 3]
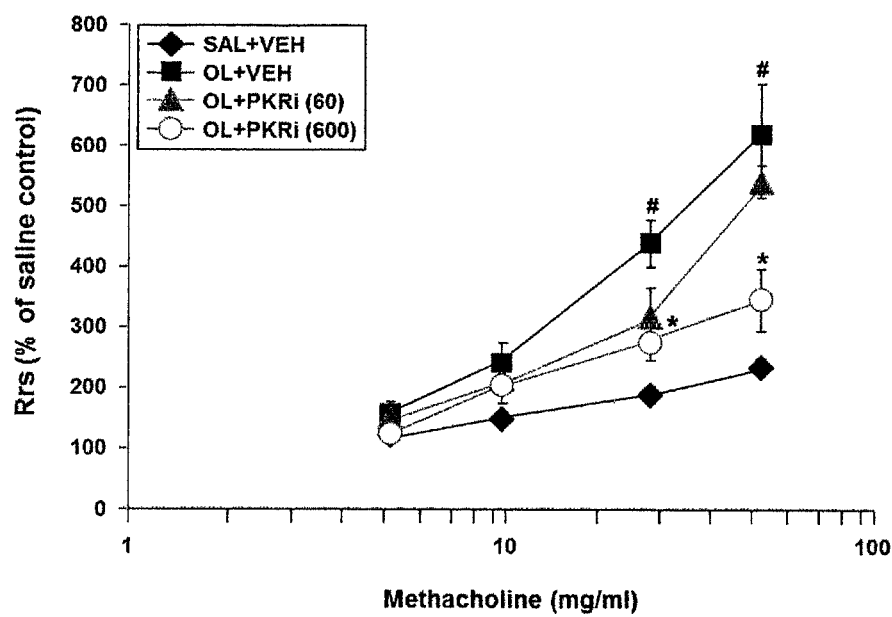

[Fig. 4a]
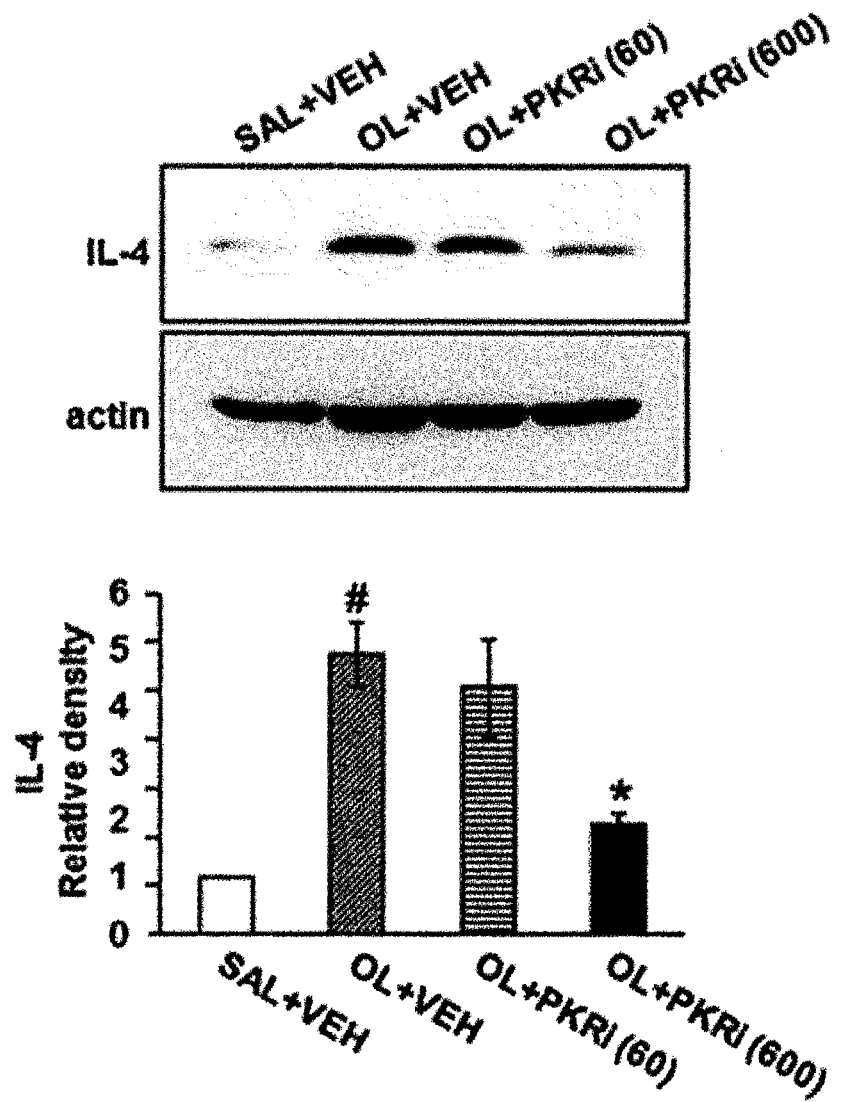

[Fig. 4b]
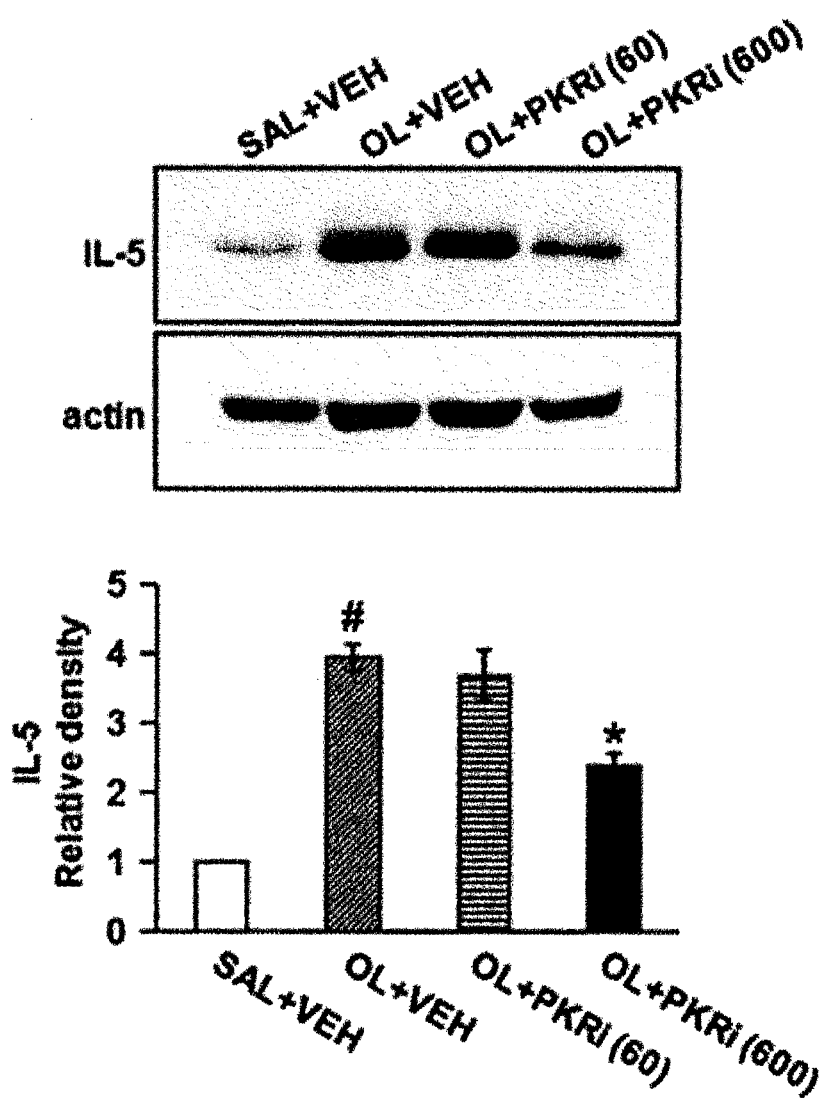

[Fig. 4c]
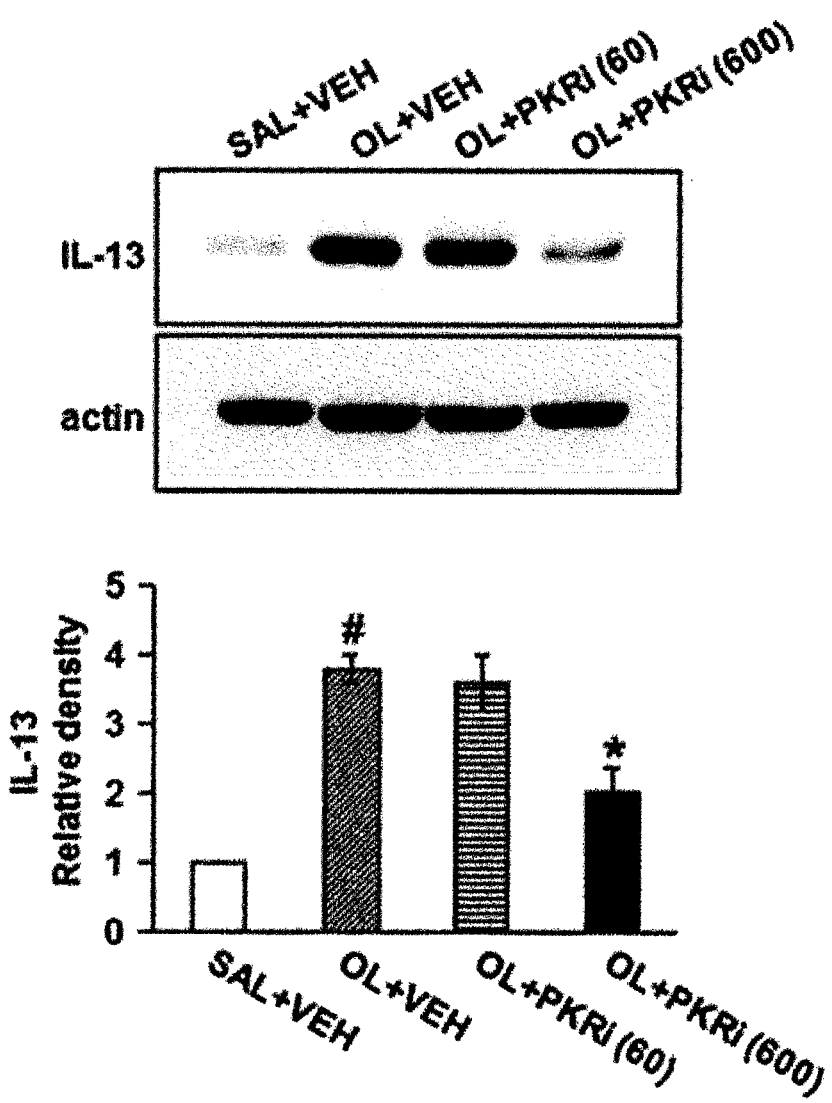

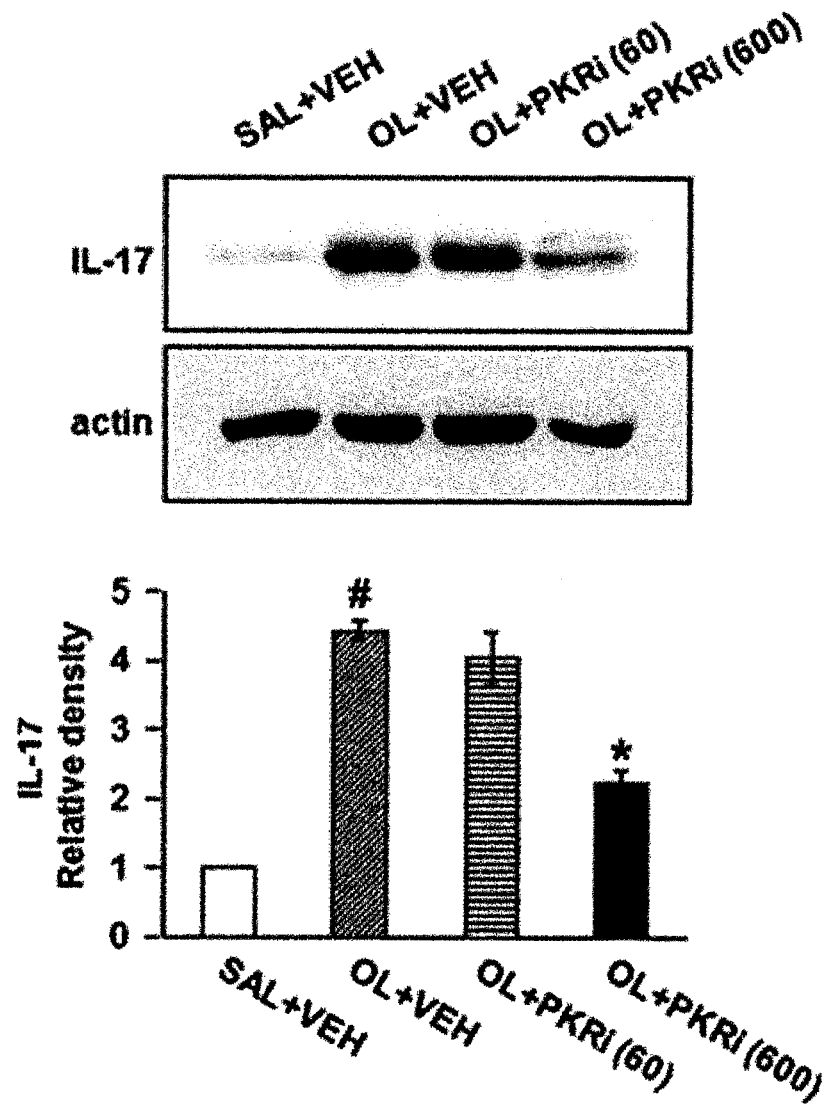
[Fig. 4d]

[Fig. 4e]
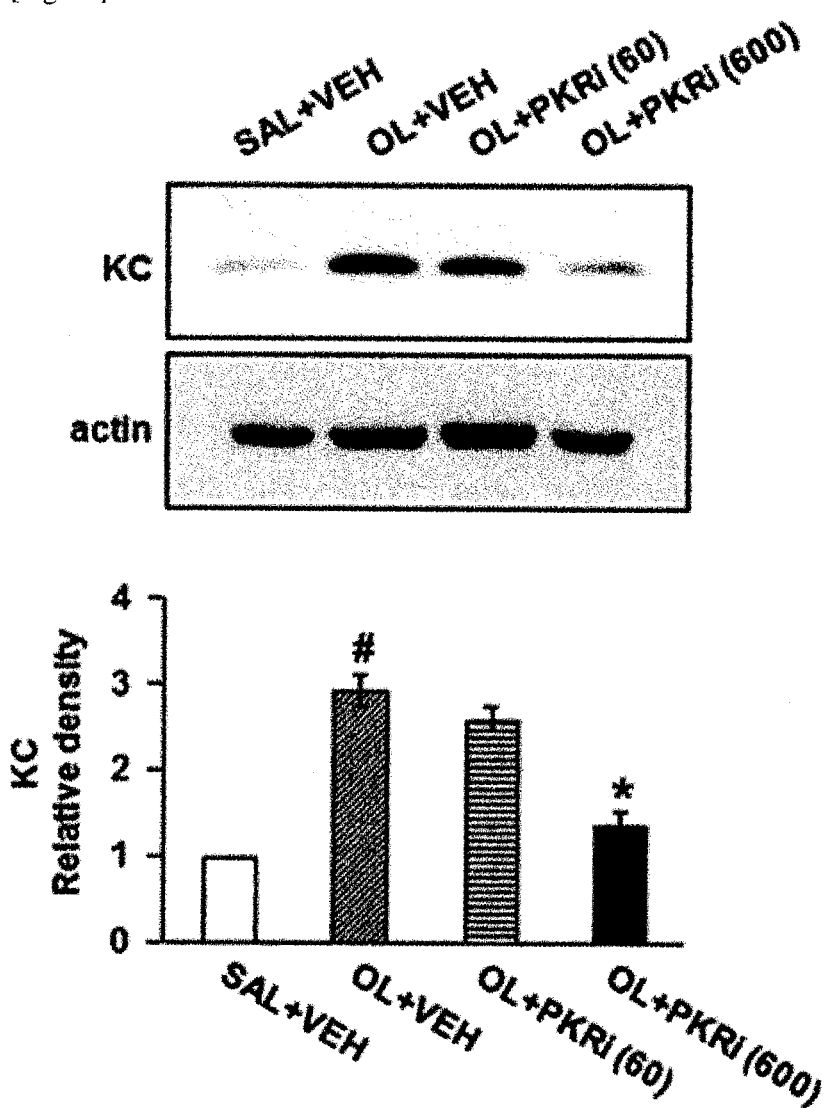

COMPOSITION FOR PREVENTION OR TREATMENT OF BRONCHIAL ASTHMA COMPRISING PKR INHIBITOR AS ACTIVE INGREDIENT

TECHNICAL FIELD

The present invention relates to a composition for preventing or treating bronchial asthma, comprising an RNA-dependent protein kinase (PKR) inhibitor or a derivative thereof as an active ingredient.

BACKGROUND ART

Bronchial asthma is a chronic disease characterized by bronchial hyperresponsiveness and intermittent airway constriction due to chronic airway inflammation, thereby causing symptoms of respiratory distress, and it is known that there is no complete cure for bronchial asthma. Bronchial asthma is a very common disease that occurs in about 5 to 10% of the total population in the majority of countries around the world, including the Republic of Korea. Recently, the prevalence of bronchial asthma has increased globally with environmental changes.

Asthma is an allergic disorder, characterized by chronic airway inflammation and bronchial hyperresponsiveness. However, it has been recently reported that asthma is associated with various pathophysiological conditions as well as irreversible pathological changes of airway tissue. In this case, persistent inflammation leads to acute and chronic airway and lung damage and consequently to common pathophysiological processes characterized by inflammation and fibrosis, and these various pathological changes are collectively referred to as airway remodeling in asthma. At present, there are no effective medications for these changes, resulting in a pathological cause of severe asthma. For typical asthma, from a pathophysiological point of view, asthma is recognized as an inflammatory disease caused by proliferation, differentiation and activation of inflammatory cells by cytokines produced by T-helper type 2 (Th2) cells, followed by migration and infiltration into the airway and surrounding tissues. In this case, it is known that inflammatory cells, such as activated eosinophils, mast cells, alveolar macrophages, etc., secrete various inflammatory mediators to induce bronchoconstriction and eosinophilia, and an increase in inflammatory mediators produced by eosinophils is an important factor in aggravating asthma. Therefore, asthma medications that have been developed and used are mainly aimed at suppressing the production of Th2 cytokines such as interleukin-4, interleukin-5, interleukin-13, etc. which are involved in production and activation of inflammatory cells in lung tissues, thereby inducing inhibition of airway inflammation (lymphocytes, eosinophils, neutrophils).

Inhaled steroids, which are used as one of the most effective medications, are effective for typical asthma, but not for steroid-resistant asthma or severe asthma that accounts for 5-15% of all patients. These patients have little response to the medications used and thus are hard to treat, unlike other patients. Patients with asthma that is not satisfactorily controlled despite the use of various medications including these inhaled steroids are defined as severe asthma, refractory asthma, or difficult to treat asthma, and characterized by persistent symptoms, frequent acute exacerbations, frequent use of systemic steroids, and frequent use of short-acting bronchodilators. Despite the development of various medications, the increase in prevalence of asthma and related mortality is due to the fact that there is no fundamental treatment for refractory severe asthma that is a common etiology. Therefore, recent trends in the development of asthma medications are focused on the development of drugs with mechanisms to overcome these severe asthma conditions.

Adults with this severe asthma are more likely to have neutrophilic airway inflammation than those with typical asthma, are highly likely to experience acute exacerbation, and exhibit severe inflammation unresponsive to steroids and bronchial hyperresponsiveness. Moreover, the importance of innate immunity in the occurrence of neutrophilic severe asthma has been emphasized, unlike the previous concept of the pathophysiology of allergic asthma.

Meanwhile, an RNA-dependent protein kinase (PKR) is specifically a serine/threonine kinase, which plays an important role in innate immune response that is activated upon viral infection in vivo. It has been recently reported that PKR plays its role in intracellular signalling pathways of Toll-like receptors, which are receptor systems recognizing external infectious agents, affecting immune responses in the lung; however, its therapeutic effects on diseases using biological models have not yet been evaluated.

As described above, it has not yet been investigated whether the PKR inhibitor has a therapeutic effect on severe asthma, and there have been no studies on this. Therefore, the inventors of the present invention have conducted research using the PKR inhibitor to develop a new drug having a therapeutic effect on severe asthma, and found that the PKR inhibitor has an excellent effect of treating severe asthma, thereby completing the present invention.

DISCLOSURE

Technical Problem

It is an object of the present invention to provide a composition for preventing or treating bronchial asthma, comprising a PKR inhibitor or a derivative thereof as an active ingredient.

Technical Solution

The present invention provides a composition for preventing or treating bronchial asthma, comprising a PKR inhibitor or a derivative thereof as an active ingredient.

Advantageous Effects

The PKR inhibitor or a derivative thereof according to the present invention reduces the total number of inflammatory cells, eosinophils, neutrophils, and lymphocytes in bronchoalveolar lavage fluid of mice with neutrophilic severe asthma, reduces airway inflammation and bronchial hyperresponsiveness, reduces inflammatory mediators, and thus can be used as a medicine and health functional food effective in preventing, ameliorating, or treating bronchial asthma.

DESCRIPTION OF DRAWINGS

FIG. 1 shows the effects of the PKR inhibitor of the present invention on the total number of inflammatory cells, eosinophils, neutrophils, and lymphocytes in bronchoalveolar lavage fluid of mouse models with neutrophilic severe asthma.

FIG. 2 shows the effects of the PKR inhibitor of the present invention on peribronchitis and perivasculitis in lung tissues of mouse models with neutrophilic severe asthma, observed with an optical microscope.

FIG. 3 shows the effects of the PKR inhibitor of the present invention on bronchial hyperresponsiveness in mouse models with neutrophilic severe asthma.

FIG. 4 shows the effects of the PKR inhibitor of the present invention on cytokines and chemokines in lung tissues of mouse models with neutrophilic severe asthma.

BEST MODE FOR CARRYING OUT THE INVENTION

The present invention provides a composition for preventing, ameliorating, or treating bronchial asthma, comprising an RNA-dependent protein kinase (PKR) inhibitor [6,8-Dihydro-8-(1H-imidazol-5-ylmethylene)-7H-pyrrolo [2,3-g]benzothiazol-7-one] represented by the following formula 1 or a derivative thereof as an active ingredient:

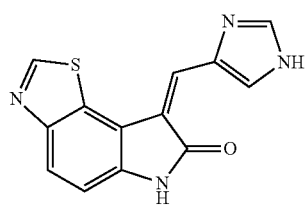

[Formula 1]

The composition comprises a pharmaceutical composition and a food composition.

Hereinafter, the present invention will be described in detail.

The RNA-dependent protein kinase (PKR) inhibitor of the present invention functions to inhibit the activity of an RNA-dependent protein kinase in vivo. The PKR inhibitor is [6,8-Dihydro-8-(1H-imidazol-5-ylmethylene)-7H-pyrrolo [2,3-g]benzothiazol-7-one] having a molecular formula of $C_3H_8N_4OS$ as shown in the above formula 1.

The PKR inhibitor or a derivative thereof according to the present invention reduces the total number of inflammatory cells, lymphocytes, neutrophils, and eosinophils in bronchoalveolar lavage fluid of mice with neutrophilic severe asthma, reduces bronchial hyperresponsiveness, and reduces Th2 cytokines and airway inflammation.

Therefore, the PKR inhibitor or a derivative thereof according to the present invention can be used as a medicine and health functional food effective in preventing, ameliorating, or treating bronchial asthma.

The bronchial asthma of the present invention includes, but not limited to, severe bronchial asthma, acute asthma, etc. In one embodiment, the severe bronchial asthma may be induced by sensitization of lipopolysaccharide (LPS) and ovalbumin (OVA).

The composition of the present invention may comprise one or more known active ingredients having the effect of preventing or treating bronchial asthma in combination with the PKR inhibitor or a derivative thereof.

The composition of the present invention may further comprise one or more pharmaceutically acceptable carriers for administration in addition to the above-described active ingredients. The pharmaceutically acceptable carrier may comprise at least one selected from the group consisting of saline, sterilized water, Ringer's solution, buffered saline, dextrose solution, maltodextrin solution, glycerol, ethanol and mixtures thereof. Other conventional additives such as antioxidants, buffers, bacteriostatics, etc. may be added, as necessary. Moreover, the composition of the present invention may be formulated into injectable dosage forms such as solutions, suspensions, emulsions, etc., pills, capsules, granules or tablets by further adding diluents, dispersants, surfactants, binders, and lubricants. Further, the composition of the present invention may be suitably formulated depending on each disease or ingredient using appropriate methods known in the art or by the method disclosed in Remington's Pharmaceutical Science (recent edition), Mack Publishing Company, Easton Pa.

The composition of the present invention may be administered orally or parenterally (for example, intravenously, subcutaneously, intraperitoneally or topically) depending on the desired method, and the dose may vary depending on a patient's weight, age, sex, health condition, diet, administration time, administration route, excretion rate, and severity of disease. The daily dose of the PKR inhibitor or a derivative thereof may be about 250 to 1000 mg/kg, preferably about 500 mg/kg, and may preferably be administered once or several times a day.

The composition of the present invention may be used alone or in combination with other therapies, including surgical therapy, hormone therapy, drug therapy and therapies using biological response modifiers for the prevention or treatment of bronchial asthma.

The composition of the present invention may be added to health functional foods for the purpose of prevention of bronchial asthma. When the PKR inhibitor or a derivative thereof according to the present invention is used as a food additive, the PKR inhibitor or a derivative thereof may be added as it is or may be used in combination with other foods or food ingredients, and may be suitably used according to conventional methods. The amount of the active ingredient to be mixed may be suitably determined depending on the intended use (prevention, health or therapeutic treatment). Generally, in the production of food or beverage, the PKR inhibitor or a derivative thereof according to the present invention may be added in an amount of 15 wt % or less, preferably 10 wt % or less, with respect to the raw material. However, in the case of long-term intake for the purposes of health and hygiene or for the purpose of health control, the amount may be less than the above range, and the active ingredient may be used in an amount exceeding the above range as there is no safety problem.

There is no particular limitation on the type of food. Examples of food to which the ingredient can be added include dairy products including meat, sausage, bread, chocolate, candies, snacks, confectionery, pizza, ramen, other noodles, gums, and ice creams, various soups, beverages, teas, drinks, alcoholic beverages, vitamin complexes, etc. and encompass all types of health functional foods in a conventional sense.

The health drink composition of the present invention may contain various flavors, natural carbohydrates, etc. as additional ingredients, like regular beverages. The above-mentioned natural carbohydrates may be monosaccharides such as glucose and fructose, disaccharides such as maltose and sucrose, polysaccharides such as dextrin and cyclodextrin, and sugar alcohols such as xylitol, sorbitol, erythritol, etc. Natural sweetening agents such as thaumatin and *stevia* extract, synthetic sweetening agents such as saccharin and aspartame, can be used as sweetening agents. The ratio of the natural carbohydrate may be generally about 0.01 to 0.20 g, preferably about 0.04 to 0.10 g per 100 ml of the composition of the present invention.

In addition to the above ingredients, the composition of the present invention may further contain various nutrients, vitamins, electrolytes, flavors, colorants, pectic acid and its salts, alginic acid and its salts, organic acids, protective colloidal thickeners, pH adjusters, stabilizers, preservatives, glycerin, alcohol, carbonating agents used in carbonated beverages, etc. In addition, the composition of the present invention may contain fruit flesh for the production of natural fruit juices, fruit juice beverages and vegetable beverages. These ingredients can be used alone or in combination. The ratio of such additives is not critical, but is generally selected in the range of 0.01 to 0.20 parts by weight per 100 parts by weight of the composition of the present invention.

MODE FOR INVENTION

Hereinafter, preferred Examples of the present invention will be provided to facilitate understanding of the present invention. However, the following Examples are provided only for better understanding of the present invention, and the present invention is not limited by the

EXAMPLES

Example 1

Effects of PKR Inhibitor on the Total Number of Inflammatory Cells, Lymphocytes, Neutrophils, and Eosinophils in Bronchoalveolar Lavage Fluid of Mouse Models with Neutrophilic Severe Asthma The following experiments were carried out to identify the effects of the PKR inhibitor of the present invention on the total number of inflammatory cells, lymphocytes, neutrophils, and eosinophils in bronchoalveolar lavage fluid of mouse models with neutrophilic severe asthma.

8-week old female C57BL/6 mice were purchased from Orient Bio (Sungnam, Korea) and used as experimental animals. Experimental groups were divided into 4 groups and 5 C57BL/6 mice were assigned to each group. Animals in one experimental group were inhaled with saline and treated with vehicle. Animals in the other three experimental groups were sensitized with ovalbumin (OVA) and lipopolysaccharide (LPS), followed by inhalation of ovalbumin to induce asthma. Animals with induced asthma in one experimental group were treated with vehicle 1 hour before the first inhalation of ovalbumin and 6 hours after the last inhalation of ovalbumin. Animals in the other two experimental groups were intraperitoneally administered with 60 μg/kg and 600 g/kg of the PKR inhibitor [6,8-Dihydro-8-(1H-imidazol-5-ylmethylene)-7H-pyrrolo[2,3-g]benzothiazol-7-one] a total of two times, 1 hour before the first inhalation of ovalbumin and 6 hours after the last inhalation of ovalbumin. [(1) Group of mice inhaled with saline and then treated with vehicle (SAL+VEH); (2) Group of mice sensitized and inhaled with ovalbumin and lipopolysaccharide and then treated with vehicle (OL+VEH); (3) Group of mice sensitized and inhaled with ovalbumin and then treated with a low dose of PKR inhibitor (OL+PKRi (60)); and (4) Group of mice sensitizes and inhaled with ovalbumin and then treated with a high dose of PKR inhibitor (OL+PKRi (600)].]

The airway of each mouse in the four experimental groups was intubated with a tube and then a 0.9% NaCl solution was injected through the tube and suctioned with a syringe to obtain bronchoalveolar lavage fluid of mice. Then, the total number of inflammatory cells, eosinophils, neutrophils, and lymphocytes was determined, and the results are shown in FIG. 1.

As shown in FIG. 1, it was found that the total number of inflammatory cells, eosinophils, neutrophils, and lymphocytes was reduced in bronchoalveolar lavage fluid of mice with neutrophilic severe asthma treated with the PKR inhibitor.

Example 2

Effects of PKR Inhibitor on Peribronchitis and Perivascular Inflammation in Lung Tissues of Mice with Neutrophilic Severe Asthma The following experiments were carried out to identify the effects of the PKR inhibitor of the present invention on peribronchitis and perivascular inflammation in lung tissues of mouse models with neutrophilic severe asthma.

Specifically, female C57BL/6 mice were sensitized with ovalbumin (OVA) and lipopolysaccharide (LPS), followed by inhalation of ovalbumin to induce asthma, and then euthanized after 48 hours. Then, a fixative (0.8% formalin, 4% acetic acid) was injected into organs and lungs of mice, and then the lungs were separated from the mice and fixed with 10% neutral formalin. After dehydration of the lung tissues, blocks were constructed with paraffin and cut into 4 μm thick sections using a micro-cutter. The sections were placed on glass slides and stained with H&E (hematoxylin and eosin) after removing the paraffin. The lung tissues were observed under an optical microscope at 20× magnification, and the results are shown in FIG. 2.

As shown in FIG. 2, it was found that the level of airway inflammation was significantly reduced in lung tissues of mice with neutrophilic severe asthma treated with the PKR inhibitor.

Example 3

Effects of PKR Inhibitor on Bronchial Hyperresponsiveness in Mice with Neutrophilic Severe Asthma In order to identify the effects of the PKR inhibitor of the present invention on bronchial hyperresponsiveness in mouse models with neutrophilic severe asthma, aerosol methacholine was administered into the airways of mice, and then the changes in airway function were measured. First, mice were anesthetized with pentobarbital, underwent tracheostomy, and placed on a ventilator for mechanical ventilation with a tidal volume of 10 ml/kg, a breathing rate of 150 breaths, and a positive end expiratory pressure of 2 cmH$_2$O. At the same time, the mice were administered with methacholine through the ventilator while gradually increasing the dose from 5.0 mg/ml to 50 mg/ml using a nebulizer, and the bronchial hyperresponsiveness (Rrs) was continuously measured. The bronchial hyperresponsiveness was assessed as a percentage of the basal value when the maximum of Rrs values measured at each methacholine concentration was administered to saline control, and the results are shown in FIG. 3.

As shown in FIG. 3, it was found that the airway resistance dose response curves of mouse models with neutrophilic severe asthma were shifted to the left, compared to normal mice treated with saline only, and the Rrs values were significantly increased at methacholine concentrations of 20 and 50 mg/ml, while the airway resistance dose response curves were shifted to the right in the group administered with the PKR inhibitor, compared to the group treated with vehicle only, and the Rrs values were also significantly reduced. This indicates that the PKR inhibitor reduces the bronchial hyperresponsiveness by ovalbumin and lipopolysaccharide.

Example 4

Effects of PKR Inhibitor on Cytokines and Chemokines in Lung Tissues of Mouse Models with Neutrophilic Severe Asthma The following experiments were carried out to identify the effects of the PKR inhibitor of the present invention on cytokines and chemokines in lung tissues of mouse models with neutrophilic severe asthma.

Quantitation of cytokines and chemokines was confirmed by Western blotting of the proteins in lung tissues. First, the proteins were extracted from homogenized lung tissues of mice with neutrophilic severe asthma, and samples were completed to maintain a constant concentration of protein. Then, the samples were loaded on SDS-PAGE gel and quantitated using an anti-IL-4 antibody (Serotec, UK) against IL-4, an anti-IL-5 antibody (SantaCruz Biotechnology, USA) against IL-5, anti-IL-13 and anti-IL-17 antibodies (R&D Systems, USA) against IL-13 and IL-17, and an anti-KC antibody against keratinocyte-induced chemokine (KC) (BioVision, USA), and the results are shown in FIGS. 4A to 4E.

As shown in FIGS. 4A to 4E, it was found that the increased cytokines and chemokines were reduced in lung tissues of mice with neutrophilic severe asthma treated with the PKR inhibitor.

Preparation Examples for the composition of the present invention will be described below.

Preparation Example 1

Preparation of Pharmaceutical Preparations 1-1. Preparation of Powders

| | |
|---|---|
| PKR inhibitor: | 200 mg |
| Lactose: | 100 mg |

The above ingredients were mixed and packed in airtight bags to prepare powders.

1-2. Preparation of Tablets

| | |
|---|---|
| PKR inhibitor: | 200 mg |
| Corn starch: | 100 mg |
| Lactose: | 100 mg |
| Magnesium stearate: | 2 mg |

The above ingredients were mixed and compressed into tablets according to a conventional method for preparing tables.

1-3. Preparation of Capsules

| | |
|---|---|
| PKR inhibitor: | 200 mg |
| Corn starch: | 100 mg |
| Lactose: | 100 mg |
| Magnesium stearate: | 2 mg |

The above ingredients are mixed and filled in gelatin capsules to prepare capsules according to a conventional method for preparing capsules.

1-4. Preparation of Injections

| | |
|---|---|
| PKR inhibitor: | 200 mg |
| Mannitol: | 100 mg |
| $Na_2HPO_4 \cdot 12H_2O$: | 2 mg |
| Sterile distilled water for injection: | Suitable amount |

The above ingredients were mixed in an ampoule (2 ml) to prepare injections according to a conventional method for preparing injections.

Preparation Example 2

Preparation of Food Compositions 2-1. Preparation of Healthy Foods

| | |
|---|---|
| PKR inhibitor: | 100 mg |
| Vitamin mixture: | Suitable amount |
| Vitamin A acetate: | 70 g |
| Vitamin E: | 1.0 mg |
| Vitamin B1: | 0.13 mg |
| Vitamin B2: | 0.15 mg |
| Vitamin B6: | 0.5 mg |
| Vitamin B12: | 0.2 g |
| Vitamin C: | 10 mg |
| Biotin: | 10 g |
| Nicotinic acid amide: | 1.7 mg |
| Folic acid: | 50 g |
| Calcium pantothenate: | 0.5 mg |
| Mineral mixture: | Suitable amount |
| Ferrous sulfate: | 1.75 mg |
| Zinc oxide: | 0.82 mg |
| Magnesium carbonate: | 25.3 mg |
| Potassium monophosphate: | 15 mg |
| Calcium phosphate dibasic: | 55 mg |
| Potassium citrate: | 90 mg |
| Calcium carbonate: | 100 mg |
| Magnesium chloride: | 24.8 mg |

The composition ratio of the vitamin and mineral mixtures was selected from those suitable for healthy foods as a preferred embodiment; however, the mixing ratio may be arbitrarily selected, and the above ingredients can be mixed according to a conventional method for preparing healthy foods to prepare granules, which can in turn be used for the preparation of healthy food compositions according to conventional methods.

2-2. Preparation of Healthy Drinks

| | |
|---|---|
| PKR inhibitor: | 100 g |
| Vitamin C: | 15 g |
| Vitamin E (powder): | 100 g |
| Iron lactate: | 19.75 g |
| Zinc oxide: | 3.5 g |
| Nicotinic acid amide: | 3.5 g |
| Vitamin A: | 0.2 g |
| Vitamin B1: | 0.25 g |
| Vitamin B2: | 0.3 g |
| Water: | Suitable amount |

The above ingredients are mixed according to a conventional method for preparing healthy drinks and stirred and heated at 85° C. for 1 hour, and the resulting solution is filtered and collected in a sterilized 2-L container. Then, the container is sealed and sterilized, followed by cold storage, and then used for the preparation of the health drink compositions of the present invention.

The above composition ratio was selected from those suitable for healthy drinks as a preferred embodiment; however, the mixing ratio may be arbitrarily selected depending on regional and national preferences such as classes with demand, countries with demand, intended uses, etc.

The invention claimed is:

1. A method for treating bronchial asthma comprising administering the compound represented by the following formula 1:

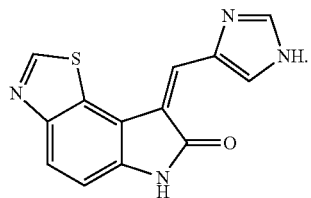

[Formula 1]

2. The method according to claim 1, wherein the bronchial asthma is severe or acute.

3. The method according to claim 1, wherein the compound reduces the number of inflammatory cells, eosinophils, neutrophils, and lymphocytes caused by asthma.

4. The method according to claim 1, wherein the compound reduces peribronchitis and perivascular inflammation caused by asthma.

* * * * *